(12) United States Patent
Kane et al.

(10) Patent No.: US 8,182,521 B2
(45) Date of Patent: May 22, 2012

(54) METHODS AND APPARATUS FOR INCREASING BLOOD CIRCULATION

(75) Inventors: John Roy Kane, Redwood City, CA (US); Scott A. Christensen, Danville, CA (US); Nathan Hamilton, Incline Village, NV (US); Stephen J. Williams, Danville, CA (US)

(73) Assignee: Dynatherm Medical Inc., Fremont, CA (US)

( * ) Notice: Subject to any disclaimer, the term of this patent is extended or adjusted under 35 U.S.C. 154(b) by 1288 days.

(21) Appl. No.: 11/830,486

(22) Filed: Jul. 30, 2007

(65) Prior Publication Data

US 2008/0021531 A1    Jan. 24, 2008

Related U.S. Application Data

(63) Continuation of application No. 11/566,575, filed on Dec. 4, 2006, now Pat. No. 8,066,752, which is a continuation of application No. 10/948,121, filed on Sep. 23, 2004, now Pat. No. 7,160,316.

(60) Provisional application No. 60/505,798, filed on Sep. 24, 2003, provisional application No. 60/821,201, filed on Aug. 2, 2006.

(51) Int. Cl.
*A61F 7/00* (2006.01)
*A61H 9/00* (2006.01)

(52) U.S. Cl. ............... 607/111; 607/104; 601/152

(58) Field of Classification Search .......... 607/111; 601/7

See application file for complete search history.

(56) References Cited

U.S. PATENT DOCUMENTS

| | | | | |
|---|---|---|---|---|
| 1,399,095 A | * | 12/1921 | Webb, Sr. | 24/1 |
| 2,082,190 A | * | 6/1937 | Vogt et al. | 601/152 |
| 2,345,073 A | * | 3/1944 | Rosett | 137/625.11 |
| 3,217,707 A | | 11/1965 | Werding | |
| 3,507,321 A | | 4/1970 | Palma | |
| 3,859,989 A | | 1/1975 | Spielberg | |
| 3,878,839 A | | 4/1975 | Norton et al. | |

(Continued)

FOREIGN PATENT DOCUMENTS

DE    19 36 113    1/1971

(Continued)

OTHER PUBLICATIONS

Morris et al., "Evidence-Based Compression: Prevention of Stasis and Deep Vein Thrombosis", Annals of Surgery 239(2), pp. 162-171, Feb. 2004, (C) 2004 Lippincott Williams & Wilkins, Inc.

(Continued)

*Primary Examiner* — Roy Gibson
*Assistant Examiner* — Kaitlyn Smith
(74) *Attorney, Agent, or Firm* — Patterson & Sheridan, LLP.

(57) ABSTRACT

A method and apparatus for the prevention of deep vein thrombosis (DVT), pulmonary embolism (PE), lower extremity edema, and other associated medical conditions by adjusting the temperature of the muscles of a foot or a leg, and/or applying vacuum or negative pressure to increase blood flow. A human extremity such as a leg is exposed to a negative pressure environment and/or a thermally controlled environment within a medical device. In one aspect, the device is portable. A thermal exchange unit and, optionally, a vacuum or negative pressure unit, are provided to increase blood flow and vasodilation. The device can be programmed by a controller in a manner to stimulate the muscles of the extremity to reduce pooling of blood therein.

23 Claims, 10 Drawing Sheets

U.S. PATENT DOCUMENTS

| | | | |
|---|---|---|---|
| 3,894,213 A | 7/1975 | Agarwala | |
| 4,149,529 A * | 4/1979 | Copeland et al. | 601/17 |
| 4,149,541 A | 4/1979 | Gammons et al. | |
| 4,186,294 A | 1/1980 | Bender | |
| 4,204,547 A | 5/1980 | Allocca | |
| 4,269,175 A * | 5/1981 | Dillon | 601/152 |
| 4,338,944 A | 7/1982 | Arkans | |
| 4,343,302 A * | 8/1982 | Dillon | 601/152 |
| 4,523,594 A | 6/1985 | Kuznetz | |
| 4,530,350 A | 7/1985 | Brown et al. | |
| 4,624,244 A | 11/1986 | Taheri | |
| 4,648,392 A | 3/1987 | Cartier et al. | |
| 4,658,823 A | 4/1987 | Beddoe et al. | |
| 4,738,249 A * | 4/1988 | Linman et al. | 601/152 |
| 4,844,072 A | 7/1989 | French et al. | |
| 5,035,003 A | 7/1991 | Rinehart | |
| 5,050,613 A | 9/1991 | Newman et al. | |
| 5,074,285 A | 12/1991 | Wright | |
| 5,149,331 A | 9/1992 | Ferdman et al. | |
| 5,183,039 A | 2/1993 | Sarian et al. | |
| 5,186,163 A * | 2/1993 | Dye | 601/27 |
| 5,230,333 A | 7/1993 | Yates et al. | |
| 5,241,951 A | 9/1993 | Mason et al. | |
| 5,241,958 A | 9/1993 | Noeldner | |
| 5,314,455 A * | 5/1994 | Johnson et al. | 607/104 |
| 5,330,519 A | 7/1994 | Mason et al. | |
| 5,344,436 A | 9/1994 | Fontenot et al. | |
| 5,369,807 A | 12/1994 | Cho et al. | |
| 5,417,720 A | 5/1995 | Mason | |
| 5,437,610 A | 8/1995 | Cariapa et al. | |
| 5,441,477 A | 8/1995 | Hargest | |
| 5,441,533 A * | 8/1995 | Johnson et al. | 607/104 |
| 5,466,250 A * | 11/1995 | Johnson et al. | 607/104 |
| 5,476,490 A | 12/1995 | Silver | |
| 5,507,792 A | 4/1996 | Mason et al. | |
| 5,575,762 A | 11/1996 | Peeler et al. | |
| 5,591,221 A * | 1/1997 | Owens | 607/111 |
| 5,620,621 A | 4/1997 | Sontag | |
| 5,634,889 A | 6/1997 | Gardner et al. | |
| 5,649,954 A | 7/1997 | McEwen | |
| 5,662,695 A | 9/1997 | Mason et al. | |
| 5,674,262 A * | 10/1997 | Tumey | 607/48 |
| 5,683,428 A | 11/1997 | Franberg et al. | |
| 5,683,438 A | 11/1997 | Grahn | |
| 5,688,225 A * | 11/1997 | Walker | 601/11 |
| 5,729,653 A | 3/1998 | Magliochetti et al. | |
| 5,746,213 A | 5/1998 | Marks | |
| 5,755,756 A | 5/1998 | Freedman, Jr. et al. | |
| 5,865,841 A | 2/1999 | Kolen et al. | |
| 5,868,690 A | 2/1999 | Eischen, Sr. | |
| 5,913,886 A | 6/1999 | Soloman | |
| 5,951,949 A | 9/1999 | Olsen | |
| 5,960,475 A | 10/1999 | Fewtrell | |
| 5,980,561 A | 11/1999 | Kolen et al. | |
| 5,997,816 A | 12/1999 | McIntosh et al. | |
| 6,135,116 A * | 10/2000 | Vogel et al. | 128/898 |
| 6,144,444 A | 11/2000 | Haworth et al. | |
| 6,149,674 A | 11/2000 | Borders | |
| 6,182,316 B1 * | 2/2001 | Thomas et al. | 5/722 |
| 6,197,045 B1 | 3/2001 | Carson | |
| 6,226,552 B1 | 5/2001 | Staunton et al. | |
| 6,238,427 B1 | 5/2001 | Matta | |
| 6,245,094 B1 | 6/2001 | Pompei | |
| 6,268,595 B1 | 7/2001 | Haenel | |
| 6,277,143 B1 | 8/2001 | Klatz et al. | |
| 6,286,144 B1 | 9/2001 | Henderson et al. | |
| 6,296,617 B1 | 10/2001 | Peeler et al. | |
| 6,319,214 B1 | 11/2001 | Wortman et al. | |
| 6,375,674 B1 | 4/2002 | Carson | |
| 6,440,093 B1 * | 8/2002 | McEwen et al. | 601/150 |
| 6,446,512 B2 | 9/2002 | Zimmerman et al. | |
| 6,461,379 B1 | 10/2002 | Carson et al. | |
| 6,488,643 B1 | 12/2002 | Tumey et al. | |
| 6,517,510 B1 | 2/2003 | Stewart et al. | |
| 6,557,704 B1 | 5/2003 | Randolph | |
| 6,565,593 B2 * | 5/2003 | Diana | 607/108 |
| 6,576,003 B2 | 6/2003 | Kotack | |
| 6,581,400 B2 | 6/2003 | Augustine et al. | |
| 6,602,277 B2 | 8/2003 | Grahn et al. | |
| 6,620,187 B2 | 9/2003 | Carson et al. | |
| 6,645,232 B2 | 11/2003 | Carson | |
| 6,648,905 B2 | 11/2003 | Hoglund et al. | |
| 6,656,208 B2 | 12/2003 | Grahn et al. | |
| 6,660,027 B2 | 12/2003 | Gruszecki et al. | |
| 6,666,879 B2 | 12/2003 | Arnold et al. | |
| 6,669,715 B2 | 12/2003 | Hoglund et al. | |
| D485,338 S | 1/2004 | Augustine et al. | |
| 6,673,099 B2 | 1/2004 | Grahn et al. | |
| 6,679,432 B1 | 1/2004 | Arnold | |
| 6,692,518 B2 | 2/2004 | Carson | |
| 6,695,872 B2 | 2/2004 | Elkins | |
| 6,699,267 B2 | 3/2004 | Voorhees et al. | |
| 6,718,785 B2 | 4/2004 | Bieberich | |
| 6,763,728 B1 | 7/2004 | Albrecht | |
| 6,764,502 B2 | 7/2004 | Bieberich | |
| 6,775,473 B2 | 8/2004 | Augustine et al. | |
| 6,786,879 B1 | 9/2004 | Bolam et al. | |
| 6,802,855 B2 | 10/2004 | Ellingboe et al. | |
| 6,827,728 B2 | 12/2004 | Ellingboe et al. | |
| 6,830,049 B2 | 12/2004 | Augustine et al. | |
| 6,840,915 B2 | 1/2005 | Augustine | |
| 6,846,294 B2 * | 1/2005 | Rastegar et al. | 601/9 |
| 6,855,158 B2 | 2/2005 | Stolpmann | |
| 6,876,884 B2 | 4/2005 | Hansen et al. | |
| 6,921,374 B2 | 7/2005 | Augustine | |
| 6,966,922 B2 | 11/2005 | Grahn et al. | |
| 6,974,428 B2 | 12/2005 | Knutson et al. | |
| 6,974,442 B2 | 12/2005 | Grahn et al. | |
| 6,987,209 B2 | 1/2006 | Augustine et al. | |
| 6,988,423 B2 | 1/2006 | Bolam et al. | |
| 7,001,416 B2 | 2/2006 | Augustine et al. | |
| 7,010,221 B2 | 3/2006 | Augustine et al. | |
| 7,014,431 B2 | 3/2006 | Hansen et al. | |
| 7,041,123 B2 | 5/2006 | Stapf et al. | |
| 7,063,676 B2 * | 6/2006 | Barak et al. | 601/150 |
| 7,074,982 B2 | 7/2006 | Knutson et al. | |
| 7,087,807 B2 | 8/2006 | Stapf | |
| 7,090,692 B1 | 8/2006 | Augustine et al. | |
| 7,100,394 B2 | 9/2006 | Bieberich et al. | |
| 7,101,389 B1 | 9/2006 | Augustine et al. | |
| 7,108,713 B1 | 9/2006 | Augustine | |
| 7,120,951 B2 | 10/2006 | Augustine et al. | |
| 7,122,046 B2 | 10/2006 | Augustine et al. | |
| 7,122,047 B2 | 10/2006 | Grahn et al. | |
| 7,164,852 B2 | 1/2007 | Cazzini et al. | |
| 7,182,776 B2 | 2/2007 | Grahn et al. | |
| 7,220,273 B2 | 5/2007 | Van Duren et al. | |
| 7,226,454 B2 | 6/2007 | Albrecht et al. | |
| 7,232,457 B2 | 6/2007 | Schmidt et al. | |
| 7,244,268 B2 | 7/2007 | Arnold et al. | |
| 7,264,630 B1 | 9/2007 | Webb | |
| 7,351,254 B2 | 4/2008 | Magers | |
| 7,361,186 B2 | 4/2008 | Voorhees et al. | |
| 7,422,576 B2 | 9/2008 | Boynton et al. | |
| 7,819,829 B1 * | 10/2010 | Chandran | 601/149 |
| 2002/0007201 A1 | 1/2002 | Grahn et al. | |
| 2002/0019653 A1 | 2/2002 | Grahn et al. | |
| 2002/0019657 A1 * | 2/2002 | Elkins | 607/111 |
| 2002/0022791 A1 | 2/2002 | Morris et al. | |
| 2002/0142894 A1 | 10/2002 | Flynn | |
| 2003/0024684 A1 | 2/2003 | Lyons et al. | |
| 2003/0040783 A1 | 2/2003 | Salmon | |
| 2003/0097163 A1 | 5/2003 | Kane et al. | |
| 2003/0125649 A1 | 7/2003 | McIntosh et al. | |
| 2003/0191437 A1 * | 10/2003 | Knighton et al. | 604/133 |
| 2004/0024322 A1 | 2/2004 | Caspers | |
| 2004/0073146 A1 | 4/2004 | Weintraub et al. | |
| 2004/0077978 A1 | 4/2004 | Nelson et al. | |
| 2004/0106884 A1 | 6/2004 | Bolam et al. | |
| 2004/0162571 A1 | 8/2004 | Rabiner et al. | |
| 2004/0223962 A1 | 11/2004 | Riordan | |
| 2005/0027218 A1 * | 2/2005 | Filtvedt et al. | 601/152 |
| 2005/0033392 A1 | 2/2005 | Belzidsky | |
| 2005/0065583 A1 | 3/2005 | Voorhees et al. | |
| 2005/0070954 A1 | 3/2005 | Johnson et al. | |
| 2005/0131489 A1 | 6/2005 | Gardon-Mollard | |
| 2005/0159690 A1 | 7/2005 | Barak et al. | |

| | | | |
|---|---|---|---|
| 2005/0209665 A1 | 9/2005 | Hunter et al. | |
| 2005/0222526 A1 | 10/2005 | Perry et al. | |
| 2005/0251067 A1 | 11/2005 | Terry | |
| 2005/0256556 A1 | 11/2005 | Schirrmacher et al. | |
| 2006/0016012 A1 | 1/2006 | Liu | |
| 2006/0036203 A1* | 2/2006 | Ouchene et al. | 601/151 |
| 2006/0058858 A1* | 3/2006 | Smith | 607/104 |
| 2006/0074362 A1 | 4/2006 | Rousso et al. | |
| 2006/0111766 A1 | 5/2006 | Grahn et al. | |
| 2006/0122670 A1 | 6/2006 | Grahn et al. | |
| 2006/0150792 A1 | 7/2006 | McCarthy et al. | |
| 2006/0189905 A1* | 8/2006 | Eischen | 601/152 |
| 2006/0287621 A1* | 12/2006 | Atkinson et al. | 601/151 |
| 2007/0060987 A1 | 3/2007 | Grahn et al. | |
| 2007/0123962 A1 | 5/2007 | Grahn et al. | |
| 2007/0142887 A1 | 6/2007 | Cazzini et al. | |
| 2007/0282249 A1* | 12/2007 | Quisenberry et al. | 604/23 |
| 2008/0021531 A1* | 1/2008 | Kane et al. | 607/111 |
| 2008/0058911 A1* | 3/2008 | Parish et al. | 607/104 |
| 2008/0064992 A1* | 3/2008 | Stewart et al. | 601/7 |
| 2008/0077205 A1 | 3/2008 | Cazzini | |
| 2008/0132816 A1* | 6/2008 | Kane et al. | 601/152 |
| 2008/0132976 A1* | 6/2008 | Kane et al. | 607/104 |
| 2008/0177232 A1* | 7/2008 | Knighton et al. | 604/133 |
| 2008/0208088 A1 | 8/2008 | Cazzini et al. | |
| 2008/0249593 A1 | 10/2008 | Cazzini et al. | |
| 2009/0036959 A1 | 2/2009 | Filtvedt et al. | |
| 2009/0048649 A1* | 2/2009 | Peret et al. | 607/100 |
| 2009/0069731 A1* | 3/2009 | Parish et al. | 601/150 |
| 2009/0099629 A1 | 4/2009 | Carson et al. | |
| 2009/0112298 A1 | 4/2009 | Jusiak et al. | |
| 2009/0177184 A1 | 7/2009 | Christensen et al. | |
| 2009/0312675 A1 | 12/2009 | Sampson et al. | |
| 2010/0095641 A1* | 4/2010 | Ruetenik | 54/82 |
| 2010/0137765 A1* | 6/2010 | Edelman | 602/14 |
| 2010/0210982 A1* | 8/2010 | Balachandran et al. | 601/152 |
| 2011/0021960 A1 | 1/2011 | Filtvedt et al. | |
| 2011/0152983 A1* | 6/2011 | Schirrmacher et al. | 607/104 |
| 2011/0264063 A1 | 10/2011 | Weston | |
| 2011/0301510 A1 | 12/2011 | Filtvedt et al. | |

FOREIGN PATENT DOCUMENTS

| | | |
|---|---|---|
| EP | 1 929 980 | 4/2007 |
| FR | 2544202 | 10/1984 |
| WO | WO 96/28120 | 9/1996 |
| WO | WO 98/40039 | 9/1998 |
| WO | WO 01/80790 | 11/2001 |
| WO | WO 02/085266 | 10/2002 |
| WO | WO 03/045289 | 6/2003 |

OTHER PUBLICATIONS

Frank et al., "Relative Contribution of Core and Cutaneous Temperatures to Thermal Comfort and Autonomic Responses in Humans", Journal of Applied Physiology, vol. 86, Issue 5, pp. 1588-1593, May 1999, http://jap.physiology.org/cgi/content/full/86/5/1588#BIBL.

Herrman et al., "Skin Perfusion Responses to Surface Pressure-Induced Ischemia: Implication for the Developing Pressure Ulcer", Journal of Rehabilitation Research & Development, vol. 36 No. 2, Apr. 1999, 20 pages.

De Witte et al, "Perioperative Shivering, Physiology and Pharmacology", Anesthesiology, vol. 96 No. 2, Feb. 2002, pp. 467-484, http://www.or.org/Reviews/four/review.html.

Grahn et al., "Recovery from Mild Hypothermia Can Be Accelerated by Mechanically Distending Blood Vessels in the Hand", J Applied Physiol 85(5): pp. 1643-1648, 1998.

Walsh et al., "Blood Flow, Sympathetic Activity and Pain Relief following Lumbar Sympathetic Blockade or Surgical Sympathectomy", Anesthesia Intensive Care 13(1), pp. 18-24 , Feb. 1985.

Kulkarni et al., "Negative Pressure Applied to the Foot Decreases the Body-Core: Great-Toe Temperature Gradient", Abstract, Department of Anesthesia, Stanford University, Stanford, CA, Oct. 13, 2007. http://www.asaabstracts.com/strands/asaabstracts/abstract.htm;jsessionid=370D6FEE1329050C935DFC3A4EBFB325?year=2007&index=8&absnum=1052.

Sessler, Daniel I., "Complications and Treatment of Mild Hypothermia", Anesthesiology 95(2), pp. 531-543, Aug. 2001.

Esburg et al: "Mechanical Characteristics of Human Skin Subject to Static vs Cyclic Normal Pressures". JRRD, vol. 36, No. 2, 1999, http://www.rehab.research.va.gov/jour/99/36/2/edsberg.pdf.

International Search Report dtd. Nov. 28, 2007 for EP 07 01 5200.

Michael McEwan, "Hypothermia—Physiology, Signs, Symptoms and Treatment Considerations," Search and Rescue Society of British Columbia, www.sarbc.org/hypo1.html, Oct. 28, 1995, pp. 1-6.

Eldar Soreide, et al., "A Non-Invasive Means to Effectively Restore Normothermia in Cold Stressed Individuals: A Preliminary Report," The Journal of Emergence Medicine, 1999, pp. 725-730, vol. 17, No. 4, U.S.A.

Dennis Grahn, "Hypothermia in Trauma-Deliberate or Accidental," Trauma Care '97, 10th Annual Trauma Anesthesia and Critical Care Symposium and World Exposition, May 15-17, 1997, pp. i and 1-21, Baltimore.

Office Action, U.S. Appl. No. 11/566,575 dtd Feb. 18, 2011.

Office Action, U.S. Appl. No. 11/945,999 dtd Apr. 13, 2011.

Radial Artery Access, "For Angioplasty and Stent Procedures". Texas Heart Institute. Oct. 2010.

Layton, et al. "The Radial Artery Access Site for Interventional Neuroradiology Procedures", www.ajnr.org. AJNR Am J. Neuroradiol 27:1151-51. May 2006.

DeviceTalk. Medical Device and Diagnostic Industry. "Wrist and Reward for Stents", Oct. 2010.

European Search Report. EP 08 15 3151 dated Apr. 7, 2011.

International Search Report, PCT/US2011/020601 dated Sep. 23, 2011.

European Office Action, Application No. 07015200.4 dated Oct. 5, 2011 (with EP Search Report).

Office Action, U.S. Appl. No. 11/870,780 dated Jan. 25, 2012.

* cited by examiner

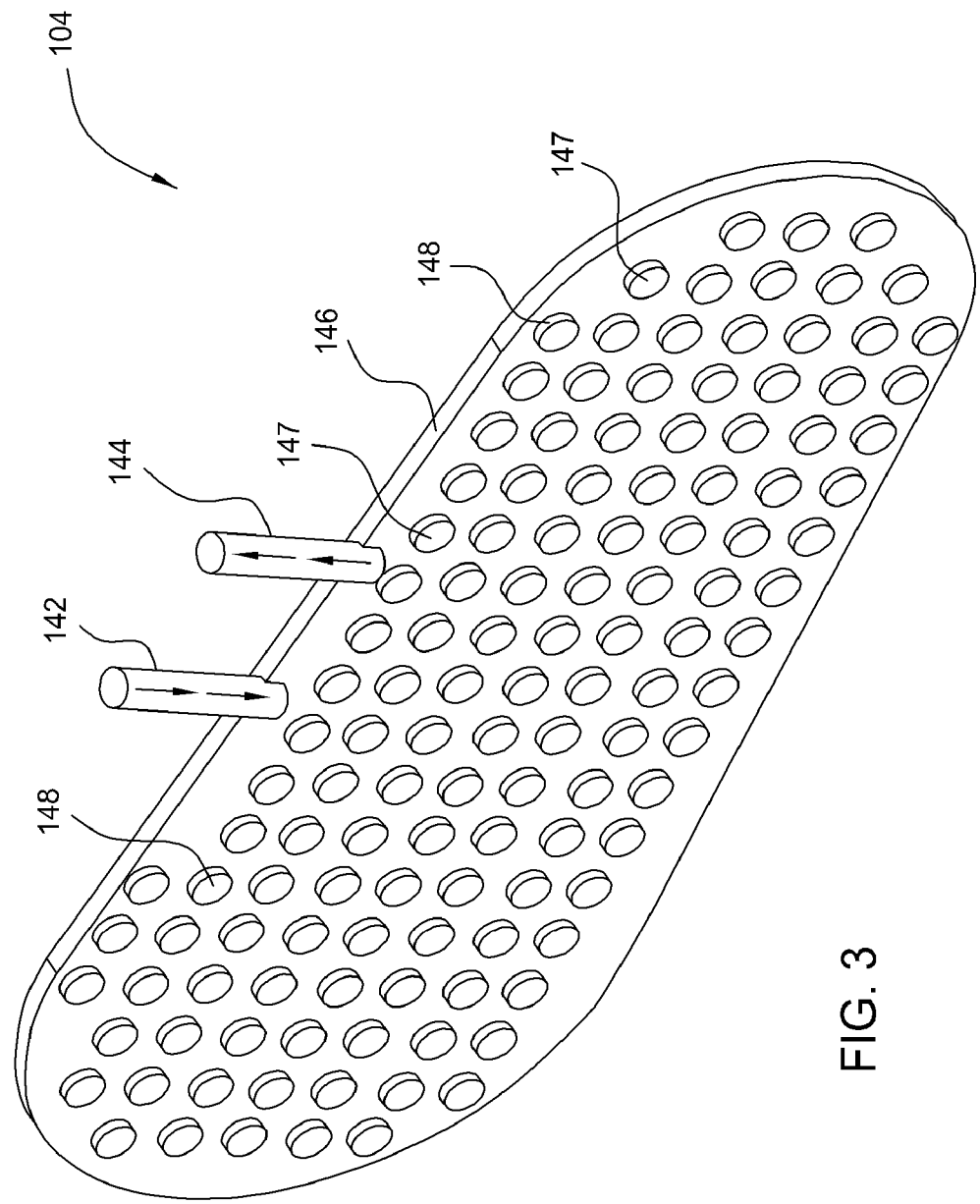
FIG. 3
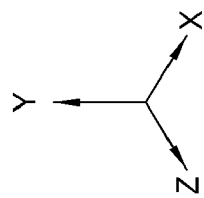

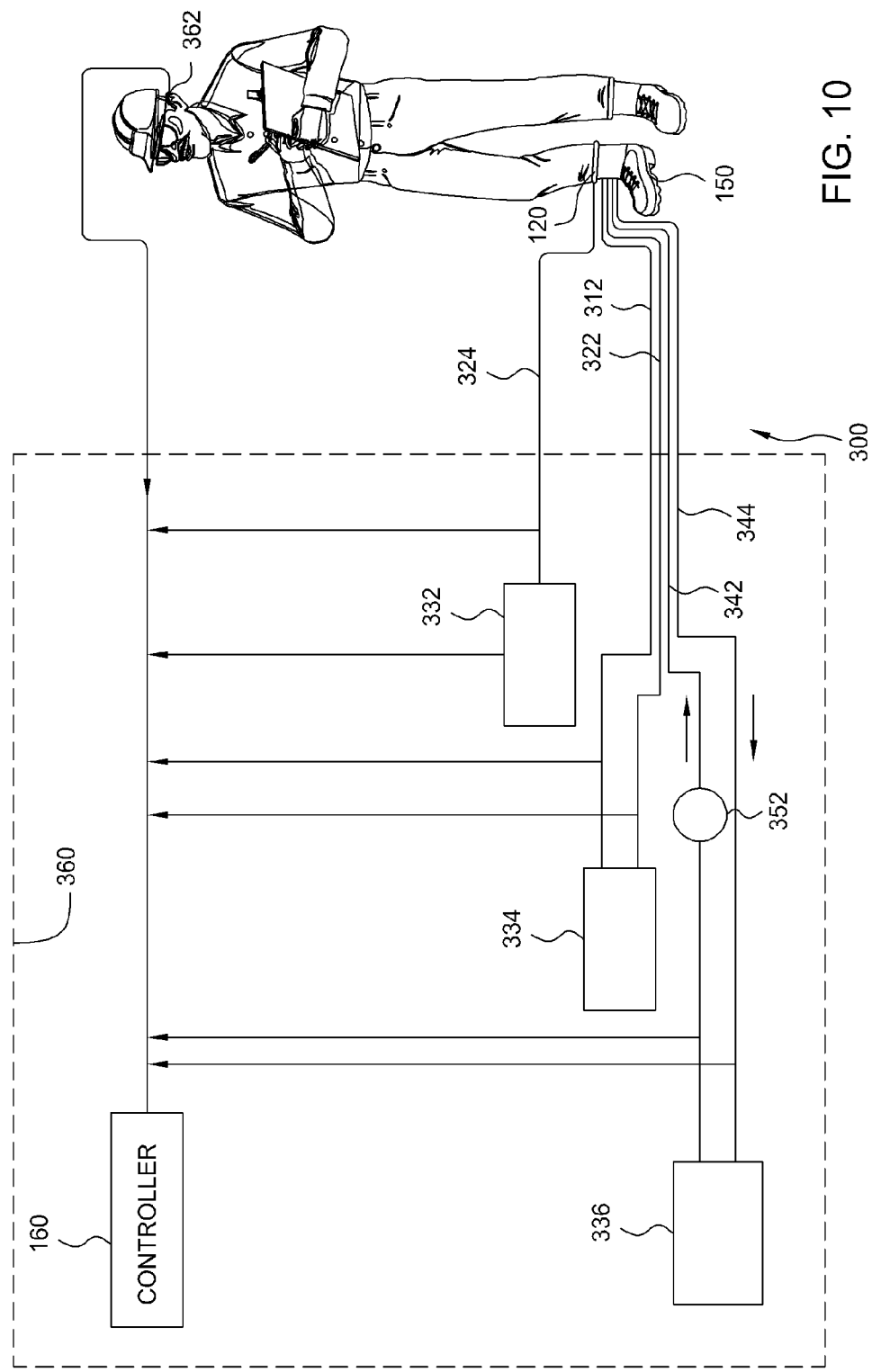

METHODS AND APPARATUS FOR INCREASING BLOOD CIRCULATION

CROSS-REFERENCE TO RELATED APPLICATIONS

This Application is a continuation-in-part of U.S. patent application Ser. No. 11/566,575, filed Dec. 4, 2006 now U.S. Pat. No. 8,066,752, which is a continuation of U.S. patent application Ser. No. 10/948,121, filed Sep. 23, 2004, now issued U.S. Pat. No. 7,160,316, issued Jan. 9, 2007, which claims benefit of U.S. provisional patent application Ser. No. 60/505,798, filed Sep. 24, 2003. This application also claims benefit of U.S. provisional patent application Ser. No. 60/821,201, filed Aug. 2, 2006. Each of the aforementioned related patent applications are herein incorporated by reference.

BACKGROUND OF THE INVENTION

1. Field of the Invention

Embodiments of the invention generally relate to methods and apparatus for increasing circulation and/or adjusting the temperature of a human. Embodiments of the invention may be used, for example, to prevent deep vein thrombosis (DVT).

2. Description of the Related Art

Venous thromboembolic disease continues to cause significant morbidity and mortality. Hospitalization in ranges of 300,000 to 600,000 persons a year is due to venous thrombosis and pulmonary embolism (PE), originating from blood clots in the veins and some clots traveling to the lung. PE is estimated to be the third most common cause of death in the United States, resulting in as many as 50,000 to 200,000 deaths a year.

Following various types of surgical procedures, as well as trauma and neurological disorders, patients are prone to developing DVT and PE. Regardless of the original reasons for hospitalization, one in a hundred patients upon admission to hospitals nationwide dies of PE. Patients suffering from hip, tibial and knee fractures undergoing orthopedic surgery, spinal cord injury, or stroke are especially at high risk. Therefore, prevention of DVT and PE is clinically important.

Studies indicated that factors contributing to the development of DVT include reduction of blood flow, vascular stasis, increase vessel wall contact time, coagulation changes, blood vessel damage, and pooling of blood in the lower extremities. It is believed that slowing of the blood flow or blood return system from the legs may be a primary factor related to DVT with greatest effect during the intraoperative phase. Also of concern is the postoperative period. Even individuals immobilized during prolong travel on an airplane or automobile may be at risk. Generally, without mobility, return of the blood back to heart is slowed and the veins of an individual rely only on vasomotor tone and/or limited contraction of soft muscles to pump blood back to the heart. One study shows that travel trips as short as three to four hours can induce DVT and PE.

Current approaches to prophylaxis include anticoagulation therapy and mechanical compression to apply pressure on the muscles through pneumatic compression devices. Anticoagulation therapy requires blood thinning drugs to clear clots in the veins which must be taken several days in advance to be effective. In addition, these drugs carry the risk of bleeding complications. Pneumatic compression devices, which mechanically compress and directly apply positive message-type pressures to muscles in the calf and foot sequentially, are not comfortable, are difficult to use even in a hospital, and are too cumbersome for mobile patients or for use during prolonged travel. In addition, most of them are heavy weighted and there are no portable or user friendly devices.

Therefore, there remains a need for an apparatus and method to increase blood flow and/or regulate body temperature in a human which can be used in reducing clots in a human extremity and preventing deep vein thrombosis.

SUMMARY OF THE INVENTION

Embodiments of the invention provide methods and apparatus for increasing blood flow and/or controlling body temperature which can be used in preventing deep vein thrombosis. In one embodiment, a lower extremity device is provided for regulating temperature and/or providing a vacuum or a negative pressure on a human extremity, such as a leg, foot, or calf of a leg, in order to increase blood flow on the human extremity and prevent deep vein thrombosis. The lower extremity device includes a hard or soft chamber body defining a hard or soft chamber therein, a vacu-seal attached to an opening of the hard or soft chamber body for contacting a human extremity therein and providing a space between the seal and the hard or soft chamber body, and one or more apertures on the hard or soft chamber body. One or more thermal exchangers, which are placed inside the lower extremity device, permanently or detachably, are connected to one or more thermal exchange lines. The one or more thermal exchangers are also connected via one or more supply lines and return line through the one or more apertures of the hard or soft chamber body to a thermal source, a heating source, a cooling source, and/or, a thermal fluid source in order to regulate the temperature to the human extremity. In addition, one or more vacuum lines can be connected through the one or more apertures of the hard or soft chamber body to one or more vacuum pumps in order to apply vacuum to the hard or soft chamber. In another embodiment, the lower extremity device can be used in combination with a mechanical compression device or the lower extremity device can itself be modified to include one or more pressure-applying pads in order to apply mechanical compression to a lower extremity of a mammal, in addition to regulating the temperature and/or applying vacuum to the lower extremity.

In still another embodiment, a method of preventing DVT includes providing a lower extremity device to a mammal, the lower extremity device comprising a hard or soft chamber body, a seal attached to an opening of the hard or soft chamber body for contacting the lower extremity therein and providing a space between the seal and the hard or soft chamber body, and one or more thermal exchangers, regulating the temperature of the lower extremity using the lower extremity device, vasodilating an arteriovenous anastomoses (AVAs) blood vessel of the lower extremity of the mammal, and reducing the constriction of the AVA blood vessel using the lower extremity device, thereby increasing blood flow of the lower extremity and decreasing clotting within the veins. The method can further include applying mechanical compression to the lower extremity of the mammal. The method may optionally include reducing the pressure of the hard or soft chamber of the lower extremity device, such as to vacuum levels.

In a further embodiment, a method of preventing DVT includes regulating the temperature of one or more extremities of a mammal and exposing the one or more extremities to a vacuum or a reduced pressure environment.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 is a perspective view of an exemplary thermal exchange unit according to one embodiment of the invention.

FIG. 10 illustrates one embodiment of a control unit connected to a device according to an embodiment of the invention.

DETAILED DESCRIPTION OF THE INVENTION

Figure 1:
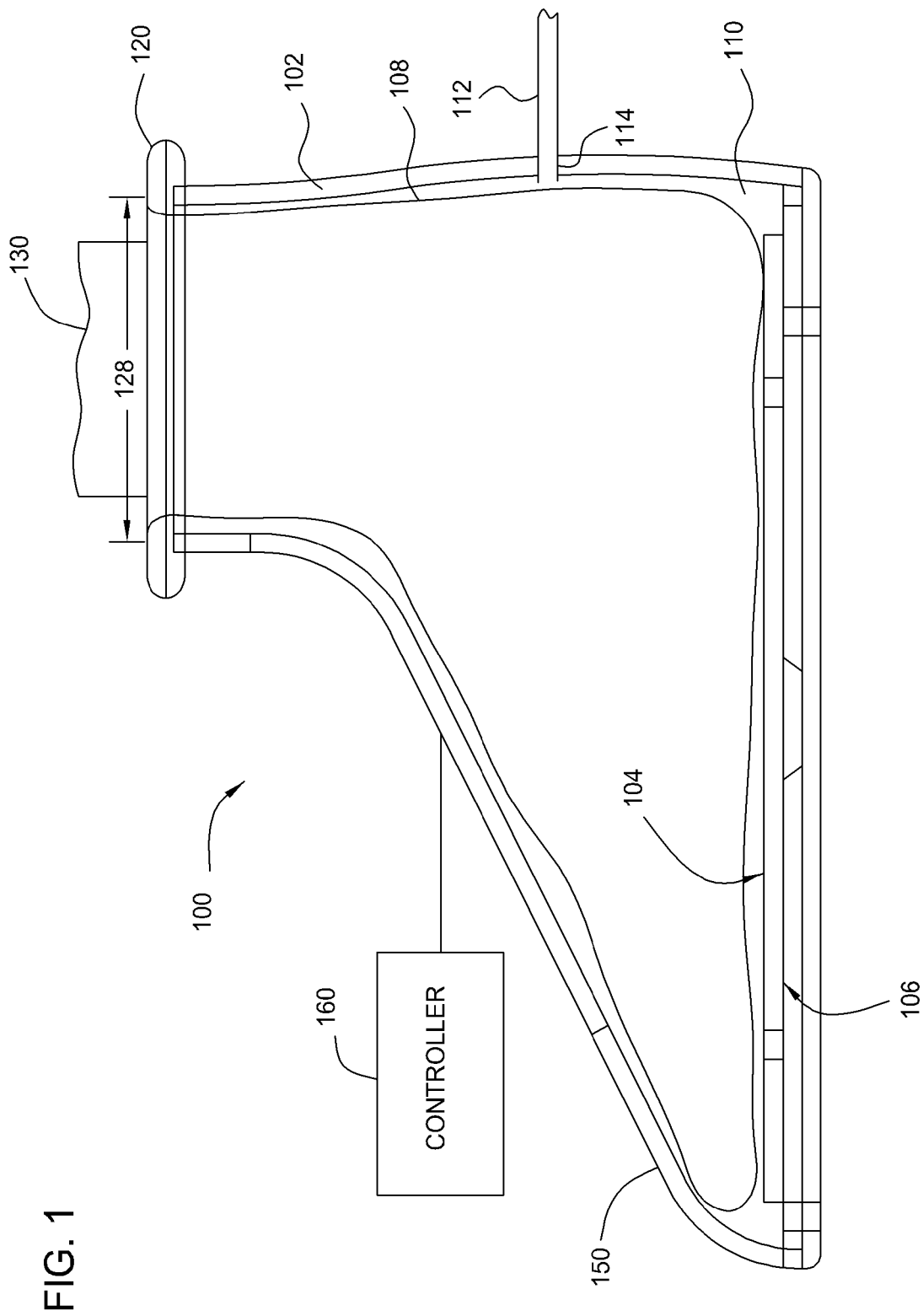
FIG. 1 is a cross-sectional view of one embodiment of an exemplary lower extremity device.

Embodiments of the invention include a method and an apparatus for preventing deep vein thrombosis (DVT). In one embodiment, an apparatus for preventing deep vein thrombosis (DVT) is provided to increase blood flow in a mammal's extremity by regulating the temperature of the mammal's extremity, vasodilating an arteriovenous anastomoses (AVAs) blood vessel of the mammal's extremity, reducing constriction of the AVA blood vessel, and/or increasing vasomotor tone. In particular, the invention provides a non-invasive, convenient apparatus for efficiently adjusting the temperature, applying vacuum, and/or applying compression pressure or forces, to the mammal's extremity to increase blood flow, promote venous blood return, and reduce blood clots.

Arteriovenous anastomoses (AVAs) are specialized blood vessels located in the palms of the hands and the soles the feet which are connected to arteries and veins. Not wishing to be bound by theory, it is believed that, by heating or preventing the temperature from cooling off, to open up the AVA vessels, reduce constriction of the AVA vessels, and increase vasomotor tone, adjusting the temperature of an extremity may increase blood flow in the AVA vessels and increase venous return pressure, thereby preventing clots in the veins and preventing DVT.

In addition, embodiments of the invention provide subjecting portions of an extremity of a mammal to a reduced pressure environment, preferably under vacuum to cause dilation of vascular structures within the portions under the reduced pressure and increase blood flow, thereby reducing venous clots and preventing DVT. Apparatus according to aspects of the invention includes a hard or soft chamber body and a vacu-seal defining a hard or soft chamber space therebetween. The pressure of the hard or soft chamber space can be regulated to a level lower than atmospheric pressure, such as a pressure level of zero mm-Hg to about −120 mm-Hg.

Generally, the apparatus to increase blood flow and prevent deep vein thrombosis (DVT) includes a hard or soft chamber body defining a hard or soft chamber therein, a vacu-seal, one or more apertures in the hard or soft chamber body, and one or more thermal exchange units attached to the hard or soft chamber body through the one or more apertures. The seal may include a sealing portion attached to an opening of the hard or soft chamber body and adapted to provide a vacuum seal for the hard or soft chamber body. The seal may further include a vacu-seal body portion adapted to contact a portion of a human extremity, resulting in a hard or soft chamber space between the seal and the hard or soft chamber body such that vacuum or reduced pressure can be applied inside the hard or soft chamber space.

In one embodiment, the hard or soft chamber body is adapted to be connected between one or more thermal sources and the thermal exchange units via one or more thermal exchange supply lines and one or more thermal exchange return lines passing through at least one aperture in the hard or soft chamber body in order to regulate or maintain the temperature of the mammal's extremity. In another embodiment, the hard or soft chamber body is connected to a vacuum port and a pump via one or more additional lines through the one or more apertures in the hard or soft chamber body in order to reduce the pressure inside the hard or soft chamber space and provide a negative pressure environment that vasodilates the vasculature of the mammal's extremity. The vasodilation of the vasculature may also help to increase the thermal exchange between the one or more thermal exchange units and the mammal's extremity.

The extremity of a mammal includes legs, feet, toes, calfs, limbs, ankles, hands, etc. While embodiments of the invention will be described further below with respect to a foot device, it is recognized that the foot device described below may be adapted for use with other extremities that have vasculature structures suitable for the vasodilation methods described herein. Regulating the temperature of the mammal's extremity may include elevating and/or maintaining the temperature. The mammal may be a human or other mammal. People at high risk of DVT, PE and other conditions, such as edema, wound swelling, venous stasis ulcers, diabetic wounds, decubitous ulcer, orthopedic surgery patients, spinal cord injured individuals, among others, can benefit from the invention.

FIG. 1 is a cross-sectional view of one embodiment of a foot device 100 and a thermal exchange unit 104. The foot device 100 includes a vacu-seal 108 and a hard or soft chamber body 102 defining a hard or soft chamber 150 to provide an enclosure in which a mammal's extremity may be positioned therein and exposed to temperature regulation and/or a vacuum environment. The thermal exchange unit 104 can be permanently or detachably placed inside the hard or soft chamber 150 to provide thermal exchange for a foot received therein.

The hard or soft chamber body 102 can be made of any durable material, such as elastomers, polycarbonates, polypropylenes, composite materials, an acrylic material, polystyrenes, high density polyethylenes (HDPE), low density polyethylenes (LDPE), poly(vinyl chloride), urethanes, polyurethanes, graphites, fiberglass, glass, rubbers, stainless steels, titanium, aluminum, light weight metal alloys (e.g., aluminum alloys, titanium alloys, etc.), polymeric materials, or any biocompatible, disposable material. The hard or soft chamber body 102 can be made of disposable low cost materials. For example, the hard or soft chamber body 102 is made of a disposable acrylic material that allows viewing of a foot positioned inside the hard or soft chamber 150. As another example, the hard or soft chamber body 102 may be made of materials that may be sterilized via autoclaving or ethylene oxide sterilization. This is especially important if the apparatus is used during surgery where sterile conditions are very important.

The vacu-seal 108 may be made of a material that is biocompatible (and therefore safe for contact with the skin of a mammal) and capable of producing an airtight seal. In one embodiment, the vacu-seal 108 is detachably disposed inside the hard or soft chamber 150. In another embodiment, the vacu-seal 108 is made of a disposable material, such as disposable liners or insert materials, to be used with a non-disposable hard or soft chamber body 102. For example, the material of the vacu-seal 108 may be polyurethane, urethane, among others. One example of the seal material is PS series thermoplastic polyurethane from Deerfield Urethane, Inc. Disposable seal materials may be manufactured and packaged such that they are sterile before use. In another embodiment, the hard or soft chamber body 102 is made of non-disposable material while the vacu-seal 108 is made of disposable material to meet health and safety requirements.

The vacu-seal 108 may include a vacu-sealing portion 120 disposed around a top opening 128 of the foot device 100 to provide a hard or soft chamber space 110 between the vacu-seal 108 and the thermal exchange unit 104. The top opening 128 is configured to receive a foot, a leg, or other extremity of a mammal. A foot disposed in the hard or soft chamber 150 is secured to the foot device 100 by the vacu-seal 108 attached to the foot device 100 through the sealing portion 120 of the vacu-seal 108 of the foot device 100.

The hard or soft chamber space 110 inside the hard or soft chamber 150 is vacu-sealed by the vacu-sealing portion 120 and adapted to be connected to a vacuum port 112 through an aperture 114 of the hard or soft chamber body 102. The vacuum port 112 is also adapted to be connected to a vacuum pump (not shown) for reducing the pressure of the hard or soft chamber space 110 inside the hard or soft chamber 150. The vacuum port 112 may be covered by a protective sheath. The position of the aperture 114 can be located near any convenient portion of the hard or soft chamber body 102. In addition, the pressure level inside the hard or soft chamber 150 can be monitored by a vacuum sensor (not shown) placed inside the hard or soft chamber space 110 with a vacuum sensor port attached to the hard or soft chamber body 102 via an aperture in the hard or soft chamber body 102.

Accordingly, the pressure inside the hard or soft chamber 150 may be regulated in a range from atmospheric pressure to sub-atmospheric levels. For example, the hard or soft chamber space 110 inside the hard or soft chamber 150 can be adjusted to a negative pressure level, such as between about zero to about −120 mmHg, or between about −20 mmHg and about −80 mmHg, when the vacu-sealing portion 120 is vacu-sealed.

One or more thermal exchange units 104 may be provided to one or more portions of the hard or soft chamber body 102 to adjust (increase, reduce, or maintain) the temperature of the foot received therein. The thermal exchange unit 104 may include a thermal-exchange fluid medium, a heated fluid, heated air, a cooled fluid, or cooled air flown therein and provided from a fluid source (not shown) via one or more fluid supply lines. Alternatively, the thermal exchange unit may include an electric pad, as described in detail in FIGS. 3-5. For example, the thermal exchange unit 104 may be a water heating pad having heated water flown therethrough. The one or more fluid supply lines and/or one or more fluid return lines having the thermal-exchange fluid medium flown therein between the thermal exchange unit 104 and the fluid source may pass through one or more apertures (not shown) or holes in the hard or soft chamber body 102. The position of the apertures for the one or more fluid supply lines and the one or more fluid return lines in the hard or soft chamber body 102 can be located near any convenient portions of the hard or soft chamber body 102 and can be close to the aperture 114 or grouped together with the vacuum port 112 for passing through the hard or soft chamber body 102 via a single aperture.

The foot device 100 may further include a controller unit 160 connected to various parts of the foot device 100 for regulating the functions of the foot device 100, including adjusting the fluid flow in and out of the thermal exchange unit 104, regulating the temperature of the thermal exchange unit 104, monitoring the pressure level inside the hard or soft chamber 150 via one or more vacuum sensors, adjusting the vacuum pump and the vacuum level inside the hard or soft chamber 150, and monitoring the temperature of the foot received in the hard or soft chamber 150, among others.

Good contact with the thermal exchange unit is important in maximizing thermal transfer to a mammal's extremity. However, the pressure differential from ambient pressure to the interior of the hard or soft chamber may cause, for example, a foot to be arched or pulled up near the sole of the foot and lose optimal contact for efficient thermal exchange. The force caused by the pressure differential is approximately equal to the area of the sole of the foot times the pressure differential. For example, the pressure differential may be approximately three pounds. In addition, the foot may be forced off the thermal exchange unit through normal jostling or positioning of the patient.

Accordingly, a flexible membrane 106 is provided between the thermal exchange unit 104 and the hard or soft chamber body 102 to enhance the surface contact between the thermal exchange unit 104 and the foot 130. The flexible membrane 106 may collapse against the thermal exchange unit 104 under a sub-atmospheric pressure or a vacuum pressure level within the hard or soft chamber 150. The flexible membrane 106 may comprise any suitable flexible material, for example, gas permeable thermoplastics, elastomeric materials, such as C-FLEX.RTM. (Consolidated Polymer Technologies, Inc., Largo, Fla.), DynaFlex (GLS Corporation, McHenry, Ill.), and other elastomeric materials with similar properties. In one embodiment, the flexible membrane 106 comprises a material that is temperature resistant.

Figure 2:
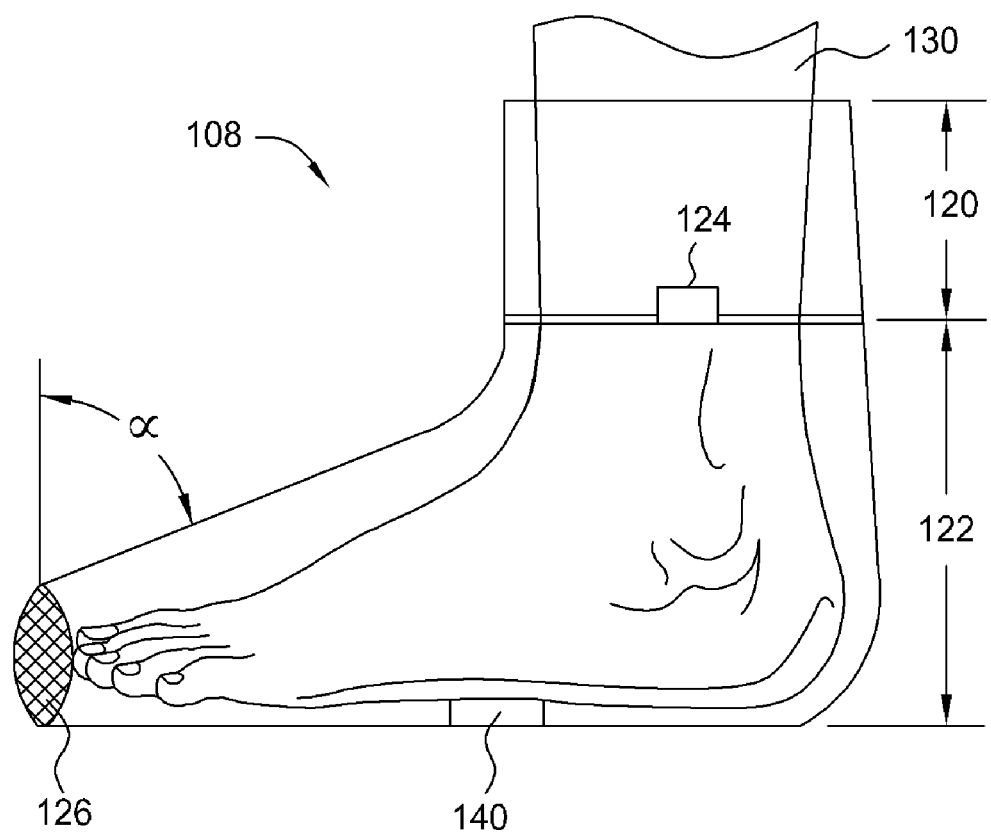
FIG. 2 is a section view of an exemplary seal having a foot disposed therein according to one embodiment of the invention.

FIG. 2 is a sectional view of the vacu-seal 108 having a foot 130 disposed therein. The vacu-seal 108 includes the vacu-sealing portion 120 and a body portion 122 which can be shaped to an extremity of a mammal, such as the foot 130 of a human. The vacu-sealing portion 120 is applied to the top opening 128 of the vacuum hard or soft chamber 150 by overlapping the vacu-seal 108 form the inside to the outside of vacuum hard or soft chamber 150. The body portion 122 may be formed to conform to the shape of the foot 130 like a sock The angle α may be less than 90°, such as between about 70° to about 90°, e.g., about 75°.

In addition, there is a hole 124 provided between the vacu-sealing portion 120 and the vacu-seal body portion 122. In one embodiment, the hole 124 is covered the ankle area of the foot 130 providing a vacuum seal between the ankle and the Vacuum hard or soft chamber. The 124 is sized to stretch (because of the material selected) to shape and size of the ankle to form a vacuum seal. There may be different shapes and sizes of the hole 124 depending on the mammal's foot.

The vacu-seal body portion 122 may include a temperature sensor 140, which is positioned in contact with the foot 130, for measuring the temperature of the foot 130. A foot disposed in the foot device 100 may rest on the vacu-seal body portion 122 above the thermal exchange unit 104. The temperature sensor 140 may be, for example, a 400 series thermistor temperature probe, available from YSI Temperature, located in Dayton, Ohio. The temperature sensor 140 is connected to the controller unit 160 of the foot device 100. In an alternative embodiment, the vacu-seal 108 may include the thermal exchange unit. In another embodiment, the vacu-seal 108 may include an in-use sensor indicating the use of the product. In addition, the in-use sensor of the vacu-seal 108 may indicate how many times the vacu-seal 108 have been used.

The vacu-seal body portion 122 may further include an air permeable portion 126, made of a permeable membrane material or a breathable material to permit the flow of air, etc. Examples of breathable materials are available from Securon Manufacturing Ltd. or 3M company. The permeable portion 126 may be positioned near any portion of the body portion to provide permeable outlets, allowing the vacuum to have the proper effect on the extremity and providing a barrier keeping the hard or soft chamber 150 from contamination for the comfort of the patient. As exemplarily shown in FIG. 2, the permeable portion 126 is positioned near the toe portions of the foot 130.

The vacu-sealing portion 120 can be wrapped around the top opening 128 of the hard or soft chamber 150 near the hole 124 of the vacu-seal 108. A pressurized seal is ultimately formed by vacu-sealing the vacu-sealing portion 120 to the hard or soft chamber 150 and pumping air out of the vacu-sealing portion 120 of the vacu-seal 108 via an air port. In addition, the air inside the hard or soft chamber 150 can be pumped out via the vacuum port 112 connected to a vacuum pump. With the vacu-sealing portion 120 properly sealed to the foot 130 under vacuum, the negative vacuum pressure applied to the hard or soft chamber 150 via the vacuum port 112 also pulls the vacu-seal 108 away from the foot 130 because $F_{vacu\text{-}seal}$ and $F_{vac}$ act in opposition to one another, thereby reducing the total force, $F_{total}$, and thus reducing the tourniquet effect. For example, a $F_{vacu\text{-}seal}$ of 80 mm Hg and a high $F_{vac}$ can reduce the $F_{total}$ to 40 mm Hg.

The vacu-seal 108 that seals the foot 130 under vacuum to the hard or soft chamber 150 plays an important role in the performance of the foot device because it prevents leakage of air into the vacuum or sub-atmospheric environment of the hard or soft chamber 150. It is recognized that the vacu-seal 108 is one example of a seal that may be used with the hard or soft chamber 150. A seal having the sealing portion with minimal leakage is preferable since it reduces the amount of air that must be continuously removed from the apparatus with an enclosed foot as vacuum is applied. However, a vacu-seal that exerts too much force on the foot may reduce or eliminate the return blood flow to the body, thus reducing the effectiveness of the foot device, and potentially creating adverse health effects. The vacu-seal 108 may also be attached to the hard or soft chamber 150 with mechanical fasteners or other fastening units. One example includes one or more mating rings which can snap into the vacuum hard or soft chamber 150. Another example includes the use of a tape with a removable liner, such as 3M removable tapes, etc., which can be removed when ready to use.

In one embodiment, the vacu-seal 108 is a single use seal. In another embodiment, the single use seal remains attached to the hard or soft chamber after use, and the hard or soft chamber and the attached seal are disposed of after a single use. In still another embodiment, the vacu-seal 108 may be removed from the hard or soft chamber and the hard or soft chamber may be used repeatedly with another vacu-seal.

In one embodiment, the vacu-sealing portion 120 may comprise a strip of releasable adhesive tape ranging from 0.5 inches to 6 inches in width, e.g., a width large enough to cover the bottom of the foot 130. The vacu-sealing portion 120 may have different widths along the interface between the vacu-sealing portion 120 and the vacu-seal body portion 122. The vacu-sealing portion 120 may comprise an adhesive face and a backing portion. The vacu-sealing portion 120 is generally long enough that when wrapped end over end around the edge of the top opening, an overlap of about 0.5 inches or larger, such as about 2 inches, is present. The overlap is preferably not to encourage the user to wrap the vacu-seal around the foot too tightly and thus create a modest vacu-sealing force, e.g., less than 20 mm Hg.

The material of the vacu-sealing portion 120 may comprise a releasable adhesive material for attachment to a mammal extremity in some portion and a more permanent adhesive in other portions thereof for attaching the vacu-seal 108 to the hard or soft chamber body 102. The releasable adhesive material may be any of a wide variety of commercially available materials with high initial adhesion and a low adhesive removal force so that the vacu-seal 108 does not pull off hair or skin and create pain when it is removed. For example, the releasable adhesive may be a single use adhesive. In addition, the adhesive material may be thick and malleable so that it can deform or give, in order to fill gaps. Adhesives with water suspended in a polymer gel, e.g., a hydrogel, are generally effective. One example of such an adhesive is Tagaderm branded 3M adhesive (part No. 9841) which is a thin (5 mm) breathable adhesive that is typically used for covering burns and wounds. Another example is an electrocardiogram (EKG) adhesive such as 3M part No. MSX 5764, which is a thicker adhesive (25 mm). The vacu-seal should fasten such that there is no leakage of the vacuum. Once a vacuum is applied, the pressure differential pulls the vacu-seal 108 closer to the foot 130 such that the vacu-seal 108 around the foot 130 is enhanced, and there is no leakage.

The backing of the vacu-sealing portion 120 may be a thin, non-elastic, flexible material. The backing supports the adhesive and keeps it from being pulled under vacuum into the appendage opening. The backing also allows the adhesive to conform to both the shape of the foot and the shape of the top opening 128 of the hard or soft chamber 150, as well as to fold in on itself to fill gaps that may be present in the vacu-seal around the foot. Furthermore, the backing prevents the adhesive from sticking to other surfaces. Commercially available polyethylene in thicknesses up to about 10 millimeters may be used for the backing. Polyethylene that is thicker than about 10 millimeters may limit the adhesive's ability to fold on itself and fill in gaps. The backing may also comprise any polymer that may be fabricated into a thin, non-elastic, flexible material.

In one embodiment, the vacu-sealing portion 120 comprises a backing surrounded by an adhesive such that the vacu-sealing portion 120 comprises two opposing adhesive faces. For example, 3M EKG adhesive product MSX 5764 contains a supportive backing in between multiple layers of adhesive. Multiple layers of backing can also be used to provide support for the vacu-seal 108.

Although an elastic backing may be used in the vacu-seal 108, an elastic support backing generally creates an inferior seal compared to a non-elastic support backing because the elastic support backing reduces the ability of the adhesive to fold against itself to fill gaps and to take up excess adhesive material. Also, the elastic backing creates a greater chance that the user will over tension the vacu-seal 108 and thereby reduce blood flow.

The top opening 128 of the hard or soft chamber 150 is preferably close to the size of the patient's foot to minimize the difference in dimensions that the vacu-seal 108 must cover. The smallest opening size that will accommodate the range of acceptable foot sizes is preferred. Minimizing the opening size reduces the force on the foot created by the pressure differential between the outside of the hard or soft chamber and the inside of the hard or soft chamber since the force caused by the pressure differential is approximately equal to the area of the top opening times the pressure differential. The vacu-seal 108 is typically able to be formed of different sizes to accommodate foot sizes down to the foot size of a small adult and up to various foot sizes of a large adult. For example, multiple opening sizes, such as small, medium, and large may be used to accommodate a wider range of foot sizes.

Alternatively, the top opening 128 may be fabricated to contract within a size range without constricting blood flow in the foot to further minimize this force and make vacu-sealing easier. For example, one or more strings may be used to tighten the top opening 128 to a foot. In another embodiment, external buckles, velcos, and straps, among others, may also be used to surround the top opening 128 of the hard or soft chamber 150 secure the top opening 128 around a foot.

In another embodiment of the invention, the hard or soft chamber 150 may be collapsible for easy storage and for ease of transportation, such as to remote locations. The collapsible hard or soft chamber may be disposable. The hard or soft chamber 150 may lay flat for storage and then expand or deploy to create a three dimensional hard or soft chamber that resists collapse by negative pressure and may be made from any flexible material including polymers such as nylons, polyesters, polystyrene, polypropylene, high density polyethylene (HDPE) or any other appropriate polymer. The flexibility of the hard or soft chamber material allows the hard or soft chamber 150 to be folded for storage and expanded for use. The hard or soft chamber may be strengthened by adding supports after expansion to prevent it from collapsing against the appendage under negative pressure.

In addition, one or more portions of the hard or soft chamber body 102 may be made from transparent materials such that the functioning of the device and the condition of the foot may be monitored during use of the device. In an alternative embodiment, the hard or soft chamber body 102 may be divided into two or more body sections to be assembled into the hard or soft chamber 150 and secured by one or more fastening units, such as velcos, snaps.

FIG. 3 is an example of the thermal exchange unit 104 of the invention. The thermal exchange unit 104 includes a thermal exchange body 146. One side of the thermal exchange body 146 includes a plurality of thermal contact domes 148 for providing thermal contact surfaces 147 directly to the vacu-seal 108 and indirectly to the foot 130. The diameter of the thermal contact surfaces 147 and the shapes or sizes thereof can vary such that the sum of the total area of the thermal contact surfaces 147 can be increase to the maximum. The thermal exchange unit 104 may further include a thermal fluid supply line 142 and a thermal fluid return line 144 connected to a thermal fluid source for circulating a thermal fluid medium therethrough the thermal exchange body 146 of the thermal exchange unit 104.

The material of the thermal exchange main body 146 may be any durable material which provides thermal conductivity for the thermal fluid medium flown therein and can be, for example, any of the materials suitable for hard or soft chamber body 102. In one embodiment, the thermal exchange main body 146 is made of a flexible material which can easily conform to the shape of the foot 130. In another embodiment, the thermal contact domes 148 are made of a rigid material to provide rigid contacts to the foot 130.

In addition, the material of the thermal contact domes 148 may be a material which provides high thermal conductivity, preferably much higher thermal conductivity than the material of the thermal exchange main body 146. For example, the thermal contact domes 148 may be made of aluminum, which provides at least 400 times higher thermal conductivity than plastics or rubber.

In one embodiment, the thermal exchange unit 104 can be formed and assembled through RF welding. In another embodiment, the thermal exchange unit 104 may be formed and assembled through injection molding. There are many possible ways to design and manufacture the thermal exchange unit to provide a flexible thermal exchange unit that does not leak.

Figure 4:
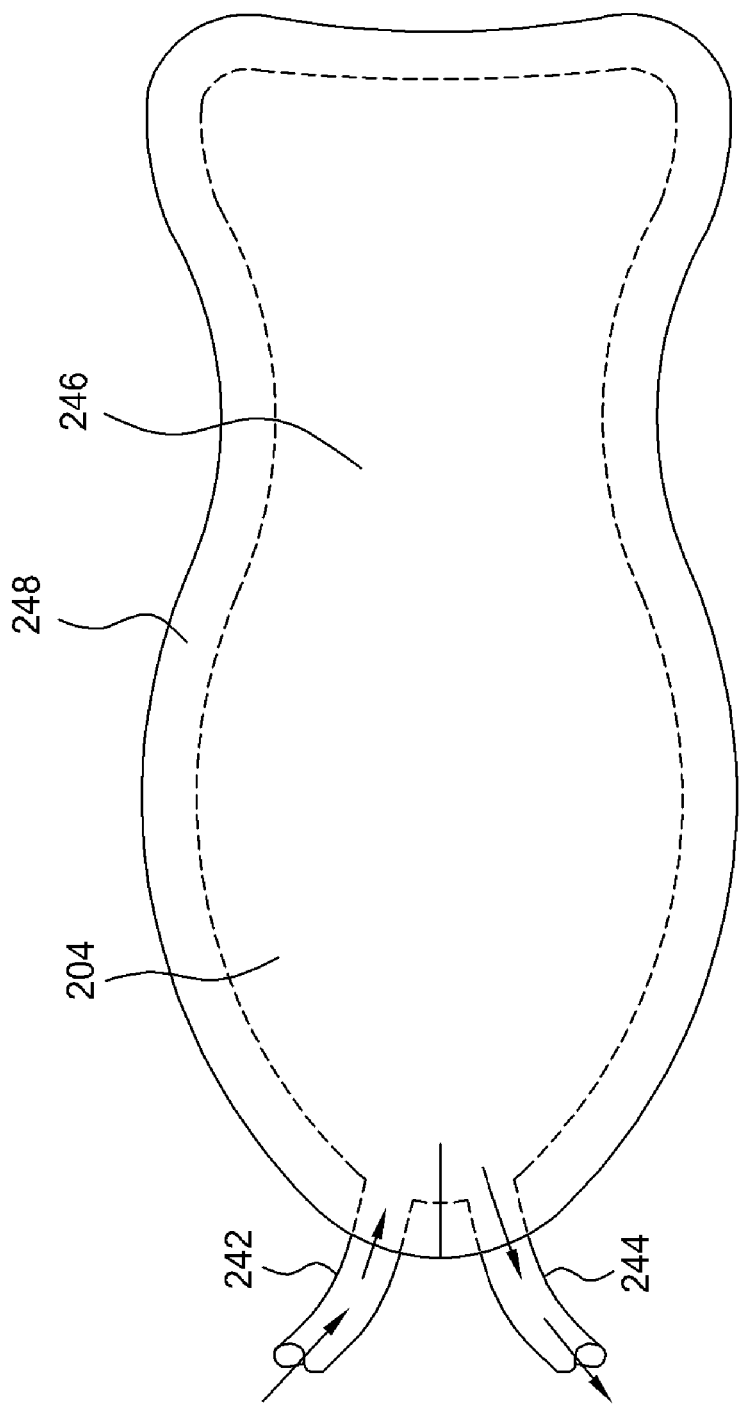
FIG. 4 is a top view of another thermal exchange unit according to another embodiment of the invention.

FIG. 4 is another example of a thermal exchange unit 204 of the invention. The thermal exchange unit 204 may include a thermal exchange body 246, a thermal fluid supply line 242 and a thermal fluid return line 244 connected to a thermal fluid source for circulating a thermal fluid medium through the thermal exchange body 246 of the thermal exchange unit 204. It is contemplated that a thermal exchange unit manufactured into layers of several materials bonded together to form internal fluid flow paths for thermal fluids to be flown therein may result in uneven surfaces, due to the presence of the internal fluid flow paths, resulting in bumpy surfaces and less contacts, thereby reducing surface area needed for maximum thermal transfer. In addition, the material for the thermal exchange main body 146, such as polyurethane, etc., may not be good conductor for thermal transfer. Thus, the thermal exchange body 246 may be covered by one or more backing sheets 248 such that flat and even contact surfaces to the foot, resulting in a large total contact area, can be provided. In addition, the backing sheet 248 can be made of high thermal conductive material to provide high thermal conductivity between the thermal exchange unit 204 and the foot 130 via the vacu-seal 108. For example, the backing sheets 248 may be made of a thin metal sheet, such as aluminum (like a foil) or other metal sheets. In general, aluminum or other metal materials may provide higher thermal conductivity than plastics or rubber, e.g., at least 400 times higher.

Figure 5:
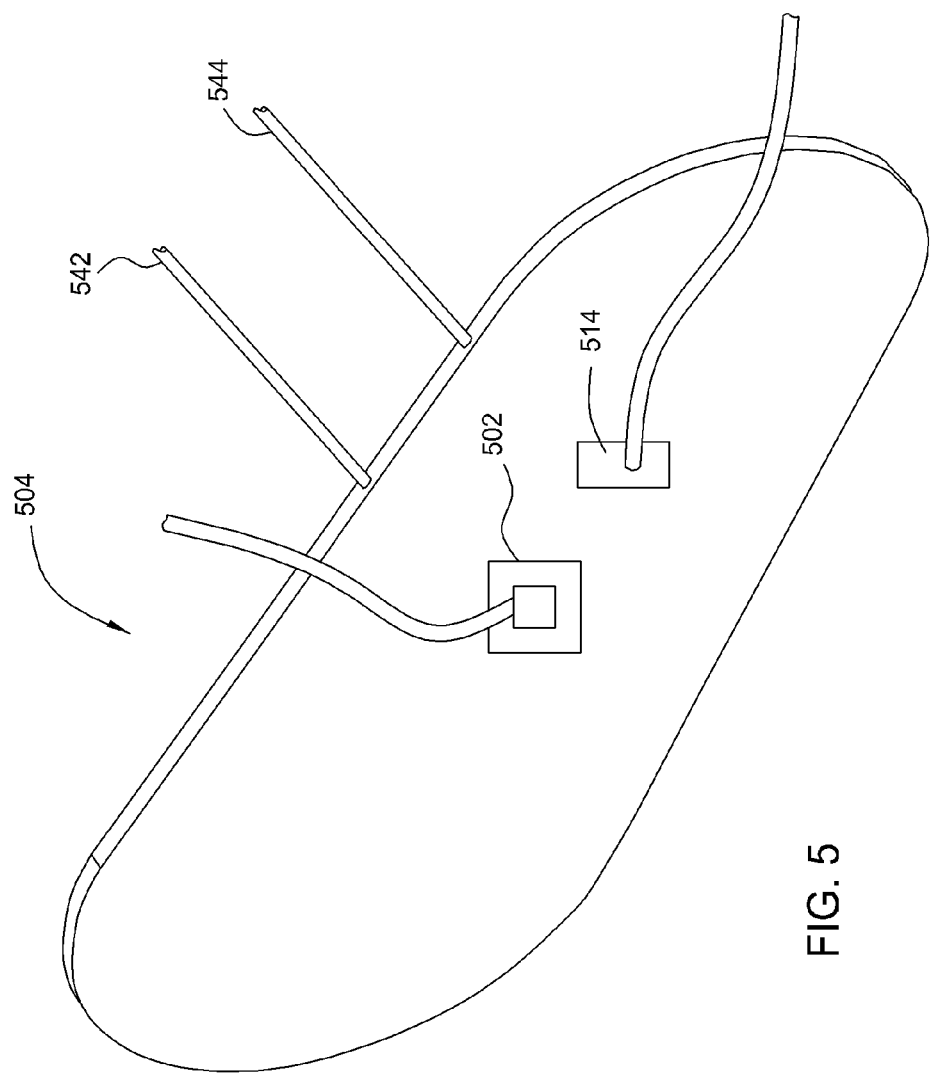
FIG. 5 is a perspective view of another thermal exchange unit according to another embodiment of the invention.

FIG. 5 is another example of a thermal exchange unit 504 of the invention. The thermal exchange unit 504 may be an electric pad having one or more electric wires 542, 544 connected to a power source. For example, the power source may be a low voltage DC current power source. In addition, the thermal exchange unit 504 may include a thermocouple 502 for monitoring the temperature and a thermoswitch 514, which can automatically shut off the electric power when the temperature of the electric pad passes a safety level.

The thermal exchange units 104, 204, 504 according to embodiments of the invention generally provide thermal exchange surfaces which heat and/or regulate the temperature of an extremity of a mammal to be kept at a temperature of about 20° C. or higher, such as between about 10° C. and about 42° C. or between about 15° C. and about 40° C. It is found that different temperatures can cause blood flow to increase at different rates depending on the temperature of the skin that the device is applied to.

It is noted that one or more thermal exchange units 104, 204, 504, individually or in combination, can be positioned and attached to one or more portions of the hard or soft chamber body 102 to provide thermal exchange and regulate the temperature of a mammal's extremity provided inside the hard or soft chamber 150. In one embodiment, one or more thermal exchange units can be pre-assembled inside the hard or soft chamber 150. In another embodiment, one or more thermal exchange units can be assembled into the hard or soft chamber 150 upon the use of a foot device.

In addition, the thermal exchange units 104, 204, 504 of the invention may include one or more temperature sensors and thermocouples to monitor the temperature of a mammal's extremity and provide temperature control feedback. For example, a tympanic temperature probe may be inserted to other body portions, such as ear canal, etc., of a mammal to monitor core body temperature and provide the core temperature feedback to the controller unit 160.

Figure 6:
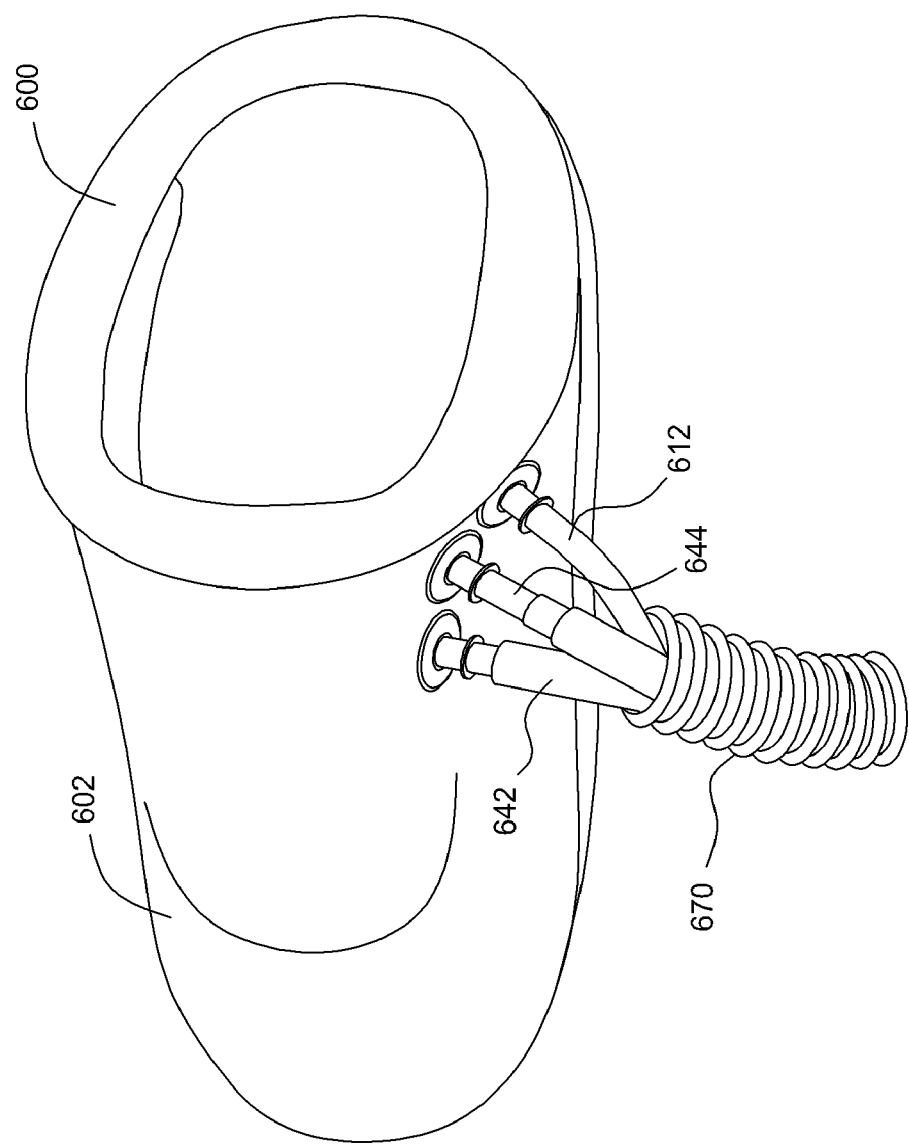
FIG. 6 is a perspective view of an exemplary foot device according to one embodiment of the invention.

FIG. 6 is a perspective view of one example of another foot device 600. The foot device 600 includes a hard or soft chamber body 602, a supply line 642, a return line 644, and a vacuum port 612. As shown in FIG. 6, one or more tubings, lines, and ports can be bundled together into a tubing set 670 and connected to a controller unit (not shown) for easy transportation and operation.

Figure 7:
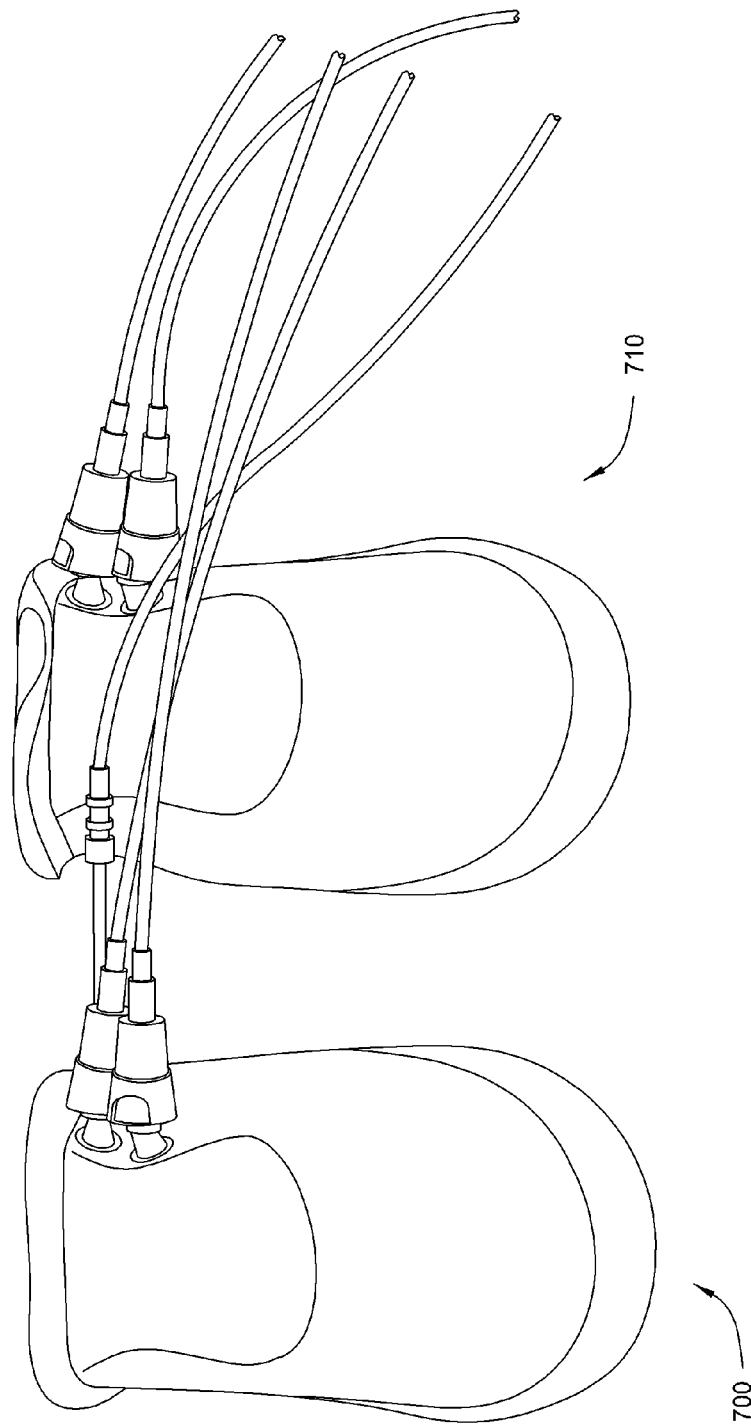
FIG. 7 is a perspective view of two exemplary foot devices according to one embodiment of the invention.

FIG. 7 is a perspective view of two exemplary foot devices 700 and 710 which can be about the same size and fitted for a right or a left foot. Alternatively, the foot devices 700 and 710 can be manufactured into different sizes suitable for various foot sizes.

Figure 8:
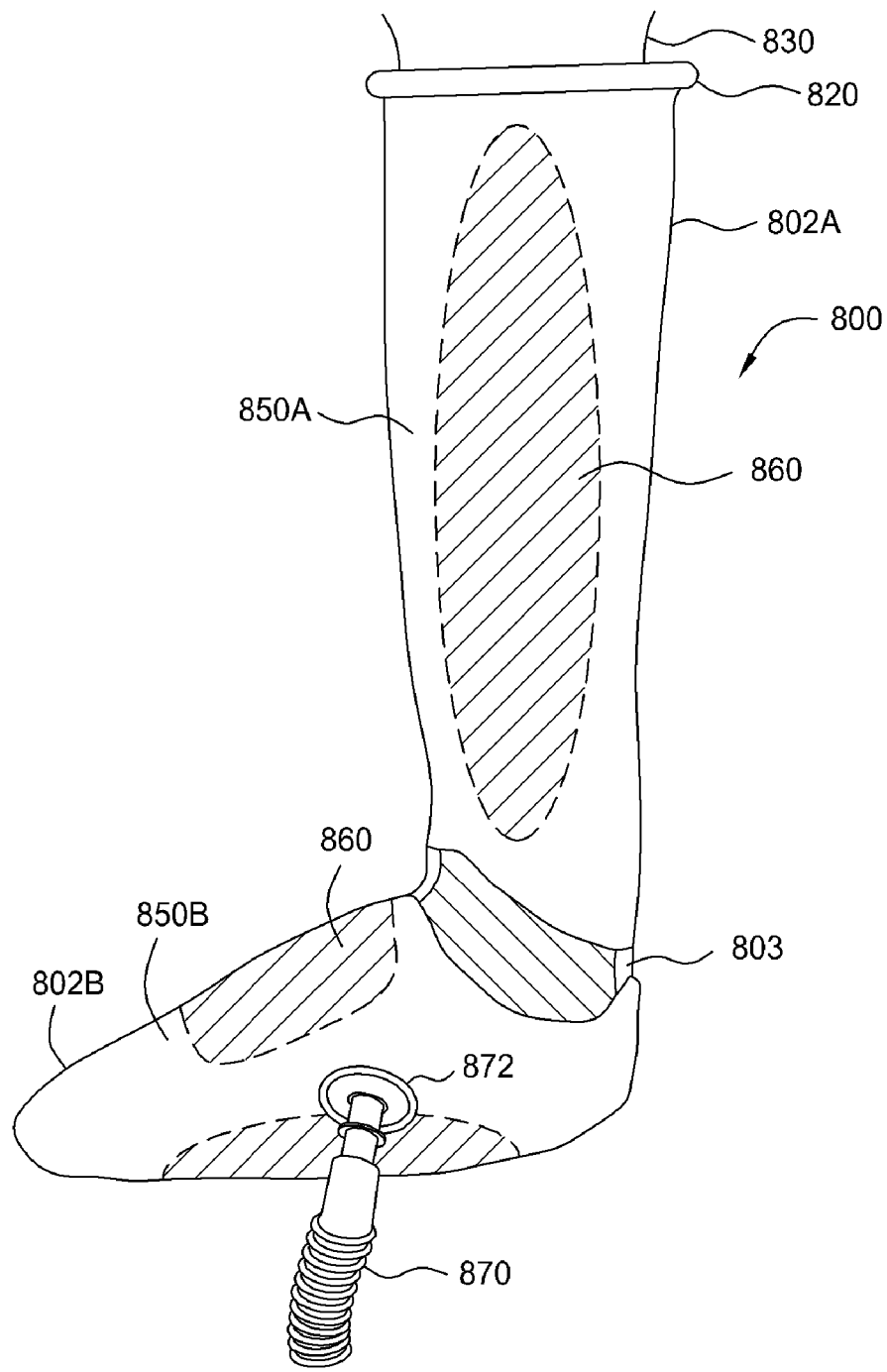
FIG. 8 is a perspective view of an exemplary leg device according to one embodiment of the invention.

FIG. 8 illustrates another example of a leg device 800 of the invention. The leg device 800 may include an upper hard or soft chamber body 802A and a lower hard or soft chamber body 802B which form an upper hard or soft chamber 850A and a lower hard or soft chamber 850B, respectively. The leg device 800 may also include a flexible portion 803, providing a flexible connection between the upper hard or soft chamber body 802A and the lower hard or soft chamber body 802B. In addition, there can be pressure air line and fluid tubing inside the flexible portion 803 connecting through the upper hard or soft chamber 850A and the lower hard or soft chamber 850B. The flexible portion 803 may be made of a flexible material to provide flexibility for a leg 830 of a mammal to be positioned inside the leg device 800. For example, the flexible portion 803 may be snugly fitted near the ankle section of the leg 830. Alternatively, the upper hard or soft chamber 850A and the lower hard or soft chamber 850B may be formed into one single vacuum hard or soft chamber. In another embodiment, the leg device 800 may include two or more individual devices, such as a foot device and a calf device, having the upper hard or soft chamber 850A and the lower hard or soft chamber 850B, respectively.

The leg device 800 may also include one or more thermal exchange units (not shown) and flexible membranes attached to one or more portions of the upper hard or soft chamber body 802A and the lower hard or soft chamber body 802B. A vacu-seal can be detachably or permanently installed inside the leg device 800 as a liner for the leg 830 and may include a vacu-sealing portion 820 near a top opening of the leg device 800 for sealing the leg device to the leg 830 under vacuum.

In addition, the leg device 800 may include one or more compression pads 860 around one or more portions of the upper hard or soft chamber 850A and the lower hard or soft chamber 850B. Each compression pad 860 may include one or more air pockets connected to gas lines and gas sources to be filled with air or various fluids when the leg 830 is positioned inside the leg device 800. In addition, the air pockets on the compression pad 860 can alternatively be pumped with air or fluids to provide a bellow-like motion to apply various compression pressures or pressurized forces on portions of the leg 830 intermittently, consecutively, or otherwise in a time appropriate manner. It is believed that applying pneumatic compression pressure or pressurized force on portions of the leg 830 may increase blood flow within the leg, prevent clotting and blood pooling in the veins, and prevent deep vein thrombosis.

One or more thermal fluid supply lines, return lines, electric lines, sensor lines, gas lines, temperature sensor ports, vacuum ports, and vacuum sensor port, can be provided to the leg device 800 via one or more apertures in the upper hard or soft chamber body 802A and/or the lower hard or soft chamber body 802B. These tubings, fluid lines, electric lines, gas lines and vacuum ports can be bundled together into a tubing set 870 through an aperture 872 on the hard or soft chamber body and connected to the controller unit 160 for easy transportation and operation.

Figure 9:
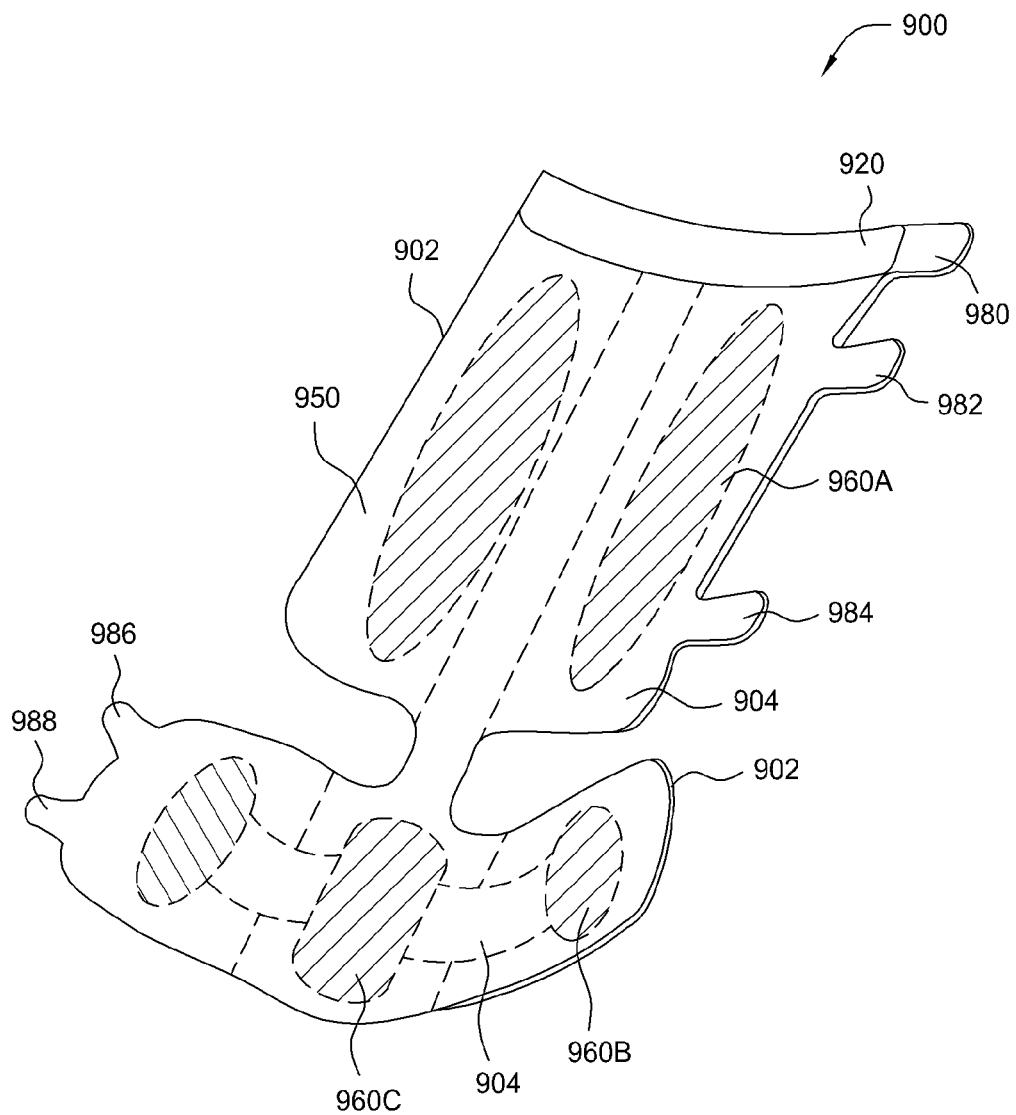
FIG. 9 is a top view of another exemplary leg device of the invention.

FIG. 9 is another example of a leg device 900 of the invention. The leg device 900 may include a hard or soft chamber body 902 and an occlusion cuff 920 proximate the top portion of the hard or soft chamber body 902. The hard or soft chamber body 902 can be conveniently assembled through fasteners 980, 982, 984, 986, 988 before or after a leg is positioned therein. The fasteners of the invention can be, for example, snaps, tabs, clips, tongs, adhesives, Velcro, among others, to join the hard or soft chamber body 902 together.

The leg device 900 may be used together with a vacu-seal having a sealing portion for attaching to the occlusion cuff 920 and providing a vacu-seal between the leg device 900 and the leg. The leg device may also be used without a vacu-seal and the occlusion cuff 920 is provided for sealing the leg device 900 to the leg.

The hard or soft chamber body 902 defines a hard or soft chamber 950 having one or more thermal exchange units 904 positioned therein. The one or more thermal exchange units 904 may be a fluid pad having a thermal fluid medium flown therein, an electric pad, or any other suitable thermal exchange units, individually or in combination. Thermal energy can be transferred from the thermal exchange unit 904 to the leg for heating or cooling the leg.

The leg device 900 further includes one or more compression pads 960A, 960B, 960C, each having one or more air pockets connected to air lines and air sources for applying pneumatic compression pressure onto portions of the leg. The one or more thermal exchange units and compression pads of the leg device 900 can be positioned overlappingly or separately on one or more portions of the hard or soft chamber body 902 inside the hard or soft chamber 950.

In operation, a foot, a leg, or a lower extremity is fitted into a vacu-seal and then the lower extremity covered with the vacu-seal is positioned in a lower extremity device. Alternatively, a detachable vacu-seal may first be assembled inside a lower extremity device before a lower extremity is fitted to the assembled lower extremity device. In addition, one or more detachable thermal exchange units may be pre-assembled inside a lower extremity device or may be assembled upon positioning a lower extremity into the lower extremity device. Then, a vacu-sealing portion of the vacu-seal is wrapped around a top opening of the foot device to form a tight seal and prevent air from entering the space between the foot and the foot device.

FIG. 10 illustrates one embodiment of the control unit 160 connected to various parts of a device 300 of the invention. A controller module 360 having the controller unit 160 therein houses all the electronics and mechanical parts which are required to regulate the temperature, vacuum pressure level, and compression pressurized force provided to the hard or soft chamber 150 of the device 300. The controller module typically includes, for example, a vacuum pump 332, a vacuum pump 334, a thermal exchange medium source 336, a fluid flow sensor 352, a thermal exchange medium pump, a heater, a cooler, thermocouples, a heating medium pump, a proportional-integral-derivative (PID) controller for process control of the vacuum and the temperature, one or more power supplies, display panels, actuators, connectors, among others, to be controlled by the controller unit 160. The settings of the controller unit 160 may be conveniently positioned onto a display panel which provides an operator interface. The controller unit 160 may contain additional electronics for optimal operation of the device 300 of the invention. In alternative embodiments, the vacuum control and temperature control may be controlled by two different controllers.

The controller unit 160 may provide safety features including a device shutdown feature that is activated if the device sensors, such as the temperature and pressure sensors, fail or become disconnected. The controller unit 160 may also include an alarm circuit or an alert signal if the temperature of the apparatus is not regulated correctly. A relief valve may be provided within the vacuum loop of the device such that the hard or soft chamber may be vented if the vacuum within the hard or soft chamber exceeds a certain level.

In one embodiment, a temperature probe 362 can be provided to measure the temperature of a portion of a mammal other than a foot, leg, or other extremity where the device is attached to. For example, a tympanic membrane can be attached to the ear canal as a temperature probe to provide core temperature reading. As such, a reference temperature for the human, such as a patient, can be obtained. Other sensors may include patient's blood flow and blood pressure and heart rate. These data are important to proper patient health care in keeping DVT from forming and keeping the patient at normal temperature range.

As shown in FIG. 10, the vacu-sealing portion 120 can be connected to the vacuum pump 332 via a vacuum port 324 to provide a vacu-seal pressure, $F_{vacu-seal}$, thereto. The hard or soft chamber 150 can be connected to the vacuum pump 334 via a vacuum port 312 and a vacuum sensor return line 322 to provide a vacuum pressure or a negative pressure inside the hard or soft chamber 150.

In addition, the hard or soft chamber having one or more thermal exchange units therein may be connected to the thermal exchange medium source 336 via a thermal exchange medium supply line 342 and a thermal exchange medium return line 344. Further, the flow of a thermal exchange medium flown inside the thermal exchange medium supply line 342 can be monitored and regulated by the fluid flow sensor 352.

These lines and ports of the invention may be bundled, contained, and strain-relieved in the same or different protective sheaths connected to the controller unit 160. The lines may also be contained in the same or different tubing set with different enclosures for each medium used, such as fluid, vacuum, electric heat, and air lines.

In one embodiment, the thermal exchange units are coupled in a closed loop configuration with the thermal exchange medium source which provides a thermal exchange medium. For example, the thermal exchange unit may be coupled in a closed liquid loop configuration with a liquid tank housed within the controller module 360. The closed loop configuration reduces the maintenance requirements for the operator because it minimizes the loss of thermal exchange medium that typically occurs if the thermal exchange unit is detached from the thermal exchange medium source. Contamination of the thermal exchange medium source is also minimized by the closed loop configuration. Contamination of the thermal exchange medium such as water can also be reduced by adding an antimicrobial agent to the thermal exchange medium source. In different embodiments, the thermal exchange medium may be either a liquid or a gas. In practice, the thermal exchange medium flow rate should be as high as possible, within practical limits of mechanics and noise. A high flow rate allows better temperature consistency, results in less thermal loss, and creates better thermal exchange. In a closed loop configuration including the thermal exchange unit and the thermal exchange medium source, with a total system volume of 0.75 liters, a flow rate of 2 liters a minute transfers twice as much fluid through the thermal exchange unit than a flow rate of 0.35 liters per minute.

In an alternative embodiment, the thermal exchange unit and vacuum lines may be connected to the control unit using actuated fittings such as quick release fittings with an automatic shut off mechanism. The automatic shut off mechanism halts the vacuum application and the heating medium flow as soon as the vacuum lines are disconnected. Actuated fittings may also allow the operator to change thermal exchange units.

The embodiments of the apparatus described above provide a method of increasing blood flow in one or more extremities of a mammal and decreasing clots within the veins in order to prevent deep vein thrombosis (DVT). The method includes providing one or more devices of the invention to the mammal and regulating the temperature of the one or more extremities of the mammal using the devices. As a result, one or more arteriovenous anastomoses (AVAs) blood vessels inside an extremity of a mammal are vasodilated, and constriction of the AVA blood vessels is reduced, thereby increasing blood flow and blood volume in the one or more extremities, decreasing the vessel wall contact time of the blood flow, and decreasing clots in the veins due to pooling. In one embodiment, a suitable portion of an extremity, preferably an extremity with vasculature that can be vasodilated by the device, such as a foot, may be placed into a device and sealed therein.

Once the foot is enclosed in the hard or soft chamber, negative pressure is applied to a vacuum port thereby lowering the pressure within the hard or soft chamber and exposing the foot to decreased pressure in the range of zero to about −120 mm-Hg, such as from about −10 mmHg to about −50 mm-Hg below atmospheric pressure. Simultaneously or sequentially, the thermal exchange medium is introduced into the thermal exchange unit positioned inside the hard or soft chamber body. The flow rate of the vacuum pump may be greater than about 4 liters per minute, and preferably about 12 liters per minute or more. In one aspect, the flow rate of the vacuum pump is between about 4 liters and about 20 liters per minute and is preferably between about 12 and about 20 liters per minute to minimize leakage of the apparatus. The negative pressure also enhances the sealing of the device by increasing the closing pressure on the sealing portion of the device and between the hard or soft chamber and the foot.

In one embodiment, the controller unit manages the thermal exchange medium and negative pressure for the duration of the treatment, which may be about 30 minutes, for example. The duration may be longer or shorter depending on the size of the foot or leg treated and the temperature of the foot or leg, and may be repeated. In some cases, the duration of the treatment may be cycled time period, for example, a time period of 1-5 minutes or longer for 5 cycles or longer. The controller is configured to halt the treatment after each treatment period. A "stop" button on the control unit may be used to turn off both the thermal exchange medium supply and the vacuum.

Embodiments of the invention may be used to increase blood flow of a patient in order to prevent DVT. Embodiments of the invention may also be used to regulate the temperature of a patient. In such a method, the temperature of the thermal exchange medium should be as high as possible without burning the patient. In a healthy patient, burning of the cells on the appendage can occur if the cell temperature exceeds about 43 degrees Celsius (° C.), but this may vary with exposure time and rate of thermal transfer. Therefore, the temperature of the thermal exchange medium is preferably calibrated such that skin temperature is maintained at less than 43 degrees Celsius. For example, different people have different tolerance levels for different temperature ranges, according to their ages, health conditions, etc. In addition, the device can be used for heating and maintaining the temperature of a patient as well as cooling. In general, a temperature range between about 10° C. to about 42° C. can be maintained.

Furthermore, the negative pressure is preferably as great as possible to maximize vasodilation, without restricting blood flow to the extremity. However, higher levels of temperature and negative pressure may cause pain in some patients because of sensitivity to temperature and sensitivity to negative pressure. Additionally, sensitivity to temperature and negative pressure may be increased with extended treatment time or repeated treatments. Furthermore, some patients may be prone to petechia, a condition in which capillaries microburst under negative pressure.

Consequently, in order to reduce patient discomfort, the controller may be configured with different temperature and vacuum settings. In one embodiment, one treatment setting is "High", which includes the highest temperature and negative pressure setting. "Medium" and "Low" settings have progressively lower settings for temperature and/or negative pressure. Patients who are at high risk for petechia or who are being treated for an extended amount of time may be treated on the "Low" setting. The vacuum setting may be adjusted to provide less negative pressure in patients that are under anesthesia since they are already vasodilated, while the temperature is kept at a higher setting. In a further aspect, the device may use between about 5 watts and about 250 watts of energy power to raise a body core temperature at a rate of between about 4° C./hour and about 12° C./hour. Preferably, the power applied is between about 5 watts and about 80 watts, although a power of up to about 250 watts may be used. In contrast, a convective warming blanket that heats the whole body may use about 500 watts.

While the foregoing is directed to embodiments of the present invention, other and further embodiments of the invention may be devised without departing from the basic scope thereof, and the scope thereof is determined by the claims that follow.

What is claimed is:

1. An apparatus for providing a therapy useful to prevent deep vein thrombosis (DVT), comprising:
    a chamber body at least partially defining an enclosed region, wherein the chamber body is adapted to flex;
    a vacu-seal comprising:
        a vacu-sealing portion disposed over an opening formed in the chamber body, wherein a surface of the vacu-sealing portion is adapted to form a seal with at least a portion of the chamber body; and
        a vacu-seal body portion coupled to the vacu-sealing portion and adapted to enclose one or more portions of a human extremity therein, wherein the vacu-seal body portion is disposed within the enclosed region and at least partially defines a space formed between a surface of the vacu-seal body portion and a surface of the chamber body;
    one or more thermal exchange units disposed within the enclosed region;
    one or more thermal exchange supply lines and one or more thermal exchange return lines attached to the one or more thermal exchange units;
    one or more apertures formed in the chamber body, wherein the one or more thermal exchange units are connected to one or more thermal sources via the one or more thermal exchange supply lines and the one or more thermal exchange return lines through at least one of the one or more apertures in the chamber body; and
    one or more compression pads for applying an intermittent compression pressure to one or more portions of the human extremity.

2. The apparatus of claim 1, wherein the chamber body comprises one or more materials selected from the group consisting of polystyrenes, high density polyethylenes (HDPE), low density polyethylenes (LDPE), poly(vinyl chloride), urethanes and polyurethanes.

3. The apparatus of claim 2, wherein the chamber body comprises a soft chamber body.

4. The apparatus of claim 1, further comprising one or more additional apertures formed in a wall of the chamber body, wherein the one or more additional apertures are adapted to connect at least one vacuum pump to the space formed between the surface of the vacu-seal body portion and the surface of the chamber body.

5. The apparatus of claim 4, wherein the at least one vacuum pump is configured to form a pressure within the space of between about zero and about −120 mm-Hg.

6. The apparatus of claim 5, further comprising a vacuum sensor port formed in a wall of the chamber body.

7. The apparatus of claim 1, wherein the chamber body and the vacu-seal are disposable.

8. The apparatus of claim 1, wherein the vacu-seal is detachably attached to the chamber body.

9. The apparatus of claim 1, wherein the one or more thermal exchange units are adapted to receive a fluid medium selected from the group consisting of heated fluids, heated air, cooled fluids, cooled air, and combinations thereof.

10. The apparatus of claim 1, wherein the one or more thermal exchange units are electric pads.

11. The apparatus of claim 1, wherein the one or more thermal exchange units are detachably placed inside the enclosed region.

12. The apparatus of claim 1, further comprising one or more flexible membranes positioned between the one or more thermal exchange units and the chamber body.

13. The apparatus of claim 1, further comprising a temperature sensor adapted to monitor the temperature of the portion of the human extremity.

14. The apparatus of claim 1, wherein the one or more portions of the human extremity is selected from the group consisting of a foot, a leg, a calf, an ankle, and any combinations thereof.

15. The apparatus of claim 1, wherein the one or more apertures are further configured to receive a vacuum port that is connected to at least one vacuum pump and to the space formed between the surface of the vacu-seal body portion and the surface of the chamber body.

16. A method of preventing deep vein thrombosis (DVT), comprising:
    disposing one or more extremities of a mammal in one or more devices, each device comprising:

a chamber body at least partially defining an enclosed region;

a vacu-seal comprising:

a vacu-sealing portion disposed over an opening formed in the chamber body, wherein a surface of the vacu-sealing portion is detachably disposed over at least a portion of the chamber body; and a vacu-seal body conjoined with the vacu-sealing portion and configured to receive a portion of the one or more extremities, wherein a space is formed between the chamber body and both the vacu-seal body and at least a portion of the vacu-sealing portion when the one or more extremities are enclosed within the vacu-seal body and the vacu-seal body and the one or more extremities are disposed in the enclosed region defined by the chamber body; and one or more thermal exchange units;

regulating the temperature of the one or more extremities of the mammal using the one or more devices, thereby vasodilating an arteriovenous anastomoses (AVAs) blood vessel in the one or more extremities of the mammal, increasing blood flow in the one or more extremities and decreasing the chance of clotting in the veins in the one or more extremities.

17. The method of claim 16, further comprising applying compression forces to a portion of the one or more extremities of the mammal.

18. The method of claim 17, wherein the compression forces are applied by one or more pressurized compression pads within the one or more devices.

19. The method of claim 17, wherein the compression forces are applied by a pressurized compression device separate from the one or more devices.

20. The method of claim 16, further comprising reducing the pressure within the enclosed region of the one or more devices.

21. The method of claim 20, wherein the pressure is reduced to a pressure between about zero and about −120 mm-Hg.

22. The method of claim 20, wherein the one or more extremities are one or more legs.

23. The method of claim 16, wherein the temperature of the one or more extremities are maintained by the one or more devices to between about 10° C. and about 42° C.

* * * * *